United States Patent
Takahashi et al.

(10) Patent No.: US 9,856,229 B2
(45) Date of Patent: Jan. 2, 2018

(54) METHOD FOR PRODUCING CYCLIC CARBONATE

(71) Applicants: NATIONAL INSTITUTE OF ADVANCED INDUSTRIAL SCIENCE AND TECHNOLOGY, Chiyoda-ku (JP); MARUZEN PETROCHEMICAL CO., LTD., Chuo-ku (JP)

(72) Inventors: Toshikazu Takahashi, Tsukuba (JP); Hiroyuki Yasuda, Tsukuba (JP); Shouji Yamamoto, Tsukuba (JP); Takashi Naniki, Ichihara (JP); Yasunori Hayashi, Ichihara (JP); Takeshi Haruna, Ichihara (JP); Takuro Furukawa, Ichihara (JP)

(73) Assignees: National Institute of Advanced Industrial Science and Technology, Chiyoda-ku (JP); MARUZEN PETROCHEMICAL CO., LTD., Chuo-ku (JP)

( * ) Notice: Subject to any disclaimer, the term of this patent is extended or adjusted under 35 U.S.C. 154(b) by 0 days.

(21) Appl. No.: 14/904,488

(22) PCT Filed: Jul. 18, 2014

(86) PCT No.: PCT/JP2014/069152
§ 371 (c)(1),
(2) Date: Jan. 12, 2016

(87) PCT Pub. No.: WO2015/008854
PCT Pub. Date: Jan. 22, 2015

(65) Prior Publication Data
US 2016/0145234 A1    May 26, 2016

(30) Foreign Application Priority Data
Jul. 19, 2013  (JP) ............... 2013-150335

(51) Int. Cl.
C07D 317/38   (2006.01)
C07D 317/36   (2006.01)
B01J 31/02    (2006.01)

(52) U.S. Cl.
CPC ........ C07D 317/38 (2013.01); B01J 31/0239 (2013.01); B01J 31/0254 (2013.01); B01J 31/0268 (2013.01); B01J 31/0269 (2013.01); C07D 317/36 (2013.01); B01J 2231/341 (2013.01); Y02P 20/142 (2015.11)

(58) Field of Classification Search
CPC .................................................. C07D 317/38
See application file for complete search history.

(56) References Cited

U.S. PATENT DOCUMENTS

| 4,226,778 | A | 10/1980 | Venturello et al. |
| 4,314,945 | A | 2/1982 | McMullen et al. |
| 5,391,767 | A | 2/1995 | Mais et al. |
| 2008/0033185 | A1 | 2/2008 | Van Kruchten et al. |
| 2008/0154052 | A1 | 6/2008 | Bolk et al. |
| 2008/0214386 | A1* | 9/2008 | Takahashi ............ B01J 31/0269 502/162 |
| 2013/0035497 | A1 | 2/2013 | Horng |

FOREIGN PATENT DOCUMENTS

| EP | 3 023 419 A1 | 5/2016 |
| JP | 55-000367 | 1/1980 |
| JP | 55-145623 | 11/1980 |
| JP | 63-017072 | 4/1988 |
| JP | 5-286965 | 11/1993 |
| JP | 2008-296066 | 12/2008 |
| WO | 2005/084801 | 9/2005 |

OTHER PUBLICATIONS

Bodner Research Web. "The Chemistry of the Halogens." © Apr. 14, 2009. Available from: <http://web.archive.org/web/20090414155348/http://chemed.chem.purdue.edu/genchem/topicreview/bp/ch10/group7.php >.*
Extended European Search Report dated Dec. 20, 2016 in Patent Application No. 14827134.9.
Jian Sun, et al., "Hydroxyl-functionalized ionic liquid: a novel efficient catalyst for chemical fixation of CO2 to cyclic carbonate," Tetrahedron Letters, vol. 49, Apr. 6, 2008, pp. 3588-3591.
Wei-Li Dai, et al., "High-Efficiency Synthesis of Cyclic Carbonates from Epoxides and CO2 over Hydroxyl Ionic Liquid Catalyst Grafted onto Cross-Linked Polymer," Catalysis Letters, vol. 197, Apr. 22, 2010, pp. 74-80.
Wei-Li Dai, et al., "Functionalized phosphonium-based ionic liquids as efficient catalysts for the synthesis of cyclic carbonate from expoxides and carbon dioxide," Applied Catalysis, vol. 470, Nov. 5, 2013, pp. 183-188.
N.N. Ezhova, et al. "Glycerol Carboxylation to Glycerol Carbonate in the Presence of Rhodium Complexes with Nitrogen-Containing Macroligands," Petroleum Chemistry, vol. 52, No. 6, Apr. 22, 2012 pp. 416-421.
International Search Report dated Sep. 30, 2014 in PCT/JP14/69152 filed Jul. 18, 2014.
English translation of the International Preliminary Report on Patentability dated Nov. 27, 2015 in PCT/JP2014/069152.

* cited by examiner

*Primary Examiner* — Noble Jarrell
*Assistant Examiner* — John S Kenyon
(74) *Attorney, Agent, or Firm* — Oblon, McClelland, Maier & Neustadt, L.L.P.

(57) ABSTRACT

Provided is a method for producing a cyclic carbonate obtained by reacting epoxide and carbon dioxide in the presence of a quaternary onium salt as a counter ion or a quaternary phosphonium salt having a halogenated anion as a counter ion, or in the presence of a solid catalyst obtained by immobilizing the quaternary onium salt onto a carrier, wherein an organohalogen compound containing at least one halogen atom in one molecule is added to the reaction system.

15 Claims, 3 Drawing Sheets

METHOD FOR PRODUCING CYCLIC CARBONATE

TECHNICAL FIELD

The present invention relates to a method for producing a cyclic carbonate.

BACKGROUND ART

Cyclic carbonates are used as organic solvents, agents for processing synthetic fibers, raw materials for medicaments, cosmetic additives and electrolyte solvents for lithium batteries, and are also utilized for the synthesis of alkylene glycols and dialkyl carbonates, and the like (Patent Literature 1), and thus are one of important compounds that are used in a wide variety of applications.

Conventionally, the cyclic carbonates have been synthesized by reacting an epoxide and carbon dioxide in the presence of a homogeneous system catalyst under a suitable pressurized condition. As such homogeneous system catalyst, halides of alkali metals and onium salts such as quaternary ammonium salts have been conventionally known (Patent Literature 2), and are industrially used.

However, in the case when such homogeneous system catalyst is used, a separation operation to separate the reaction mixture and catalyst by distillation, or the like is generally required, and thus the production steps become complex, and there are problems of the decomposition of the catalyst during the separation step and the generation of by-products.

Thus, for the purpose of simplification of a separation process of a catalyst, a heterogeneous catalyst obtained by immobilizing a quaternary phosphonium having a halogenated ion as a counter ion onto a carrier such as silica gel has been suggested (Patent Literatures 3 and 4).

However, such a heterogeneous catalyst has a problem that an immobilized quaternary phosphonium salt gradually leaches during the reaction and an amount of a catalyst that relates to the reaction is substantially reduced, resulting in decreasing the yield over time. In particular, when the above described catalyst is used in a continuous process, frequent exchange of catalysts is required because of degradation of the catalysts and heterogeneous catalysts are thus not satisfactory enough from the viewpoints of production efficiency and costs of the catalysts. Therefore, it has been demanded to suppress degradation of a catalyst due to leaching out of a quaternary phosphonium salt and to keep catalytic activity over a long period of time.

CITATION LIST

Patent Literatures

Patent Literature 1: JP S55-145623 A
Patent Literature 2: JP S63-17072 B
Patent Literature 3: WO 2005/084801 A
Patent Literature 4: JP 2008-296066 A

SUMMARY OF INVENTION

Technical Problem

An object of the present invention is to provide a method for producing a cyclic carbonate by a reaction of epoxide and carbon dioxide wherein acyclic carbonate can be effectively produced at a high conversion rate and a high yield and degradation of the catalyst over time is suppressed and catalytic activity hardly decreases.

Solution to Problem

The present inventors conducted intensive studies. As a result, they found that a cyclic carbonate can be effectively produced at a high conversion rate and a high yield by reacting epoxide and carbon dioxide after adding an organohalogen compound containing at least one halogen atom in one molecule in the presence of a specific catalyst using a quaternary onium salt, and degradation of the catalyst over time is suppressed and catalytic activity hardly decreases, and the present invention was thus completed.

That is, there is provided a method for producing a cyclic carbonate for reacting epoxide and carbon dioxide in the presence of a quaternary onium salt selected from the group consisting of a quaternary ammonium salt having a halogenated anion as a counter ion and a quaternary phosphonium salt having a halogenated anion as a counter ion, or in the presence of a solid catalyst obtained by immobilizing the quaternary onium salt onto a carrier, wherein an organohalogen compound containing at least one halogen atom in one molecule is added to the reaction system.

According to the present invention, there is provided a method for continuously producing a cyclic carbonate by filling a catalyst in a fixed bed tubular reactor and continuously supplying carbon dioxide and epoxide to the fixed bed tubular reactor to be brought into contact with the catalyst and, at the same time, continuously extracting the reaction solution contained in the fixed bed tubular reactor, wherein the producing method includes using a solid catalyst obtained by immobilizing a quaternary onium salt selected from the group consisting of a quaternary ammonium salt having a halogenated anion as a counter ion and a quaternary phosphonium salt having a halogenated anion as a counter ion onto a carrier as the catalyst, and supplying an organohalogen compound containing at least one halogen atom in the molecule to the fixed bed tubular reactor.

Advantageous Effects of Invention

According to the producing method of the present invention, acyclic carbonate can be effectively produced at a high conversion rate and a high yield and degradation of the catalyst over time is suppressed and catalytic activity hardly decreases. Therefore, according to the producing method of the present invention by a continuous flow process, a use amount of a catalyst and a renewal cost of a catalyst can be suppressed, and a cyclic carbonate can be industrially advantageously produced.

DESCRIPTION OF EMBODIMENTS

Figure 1:
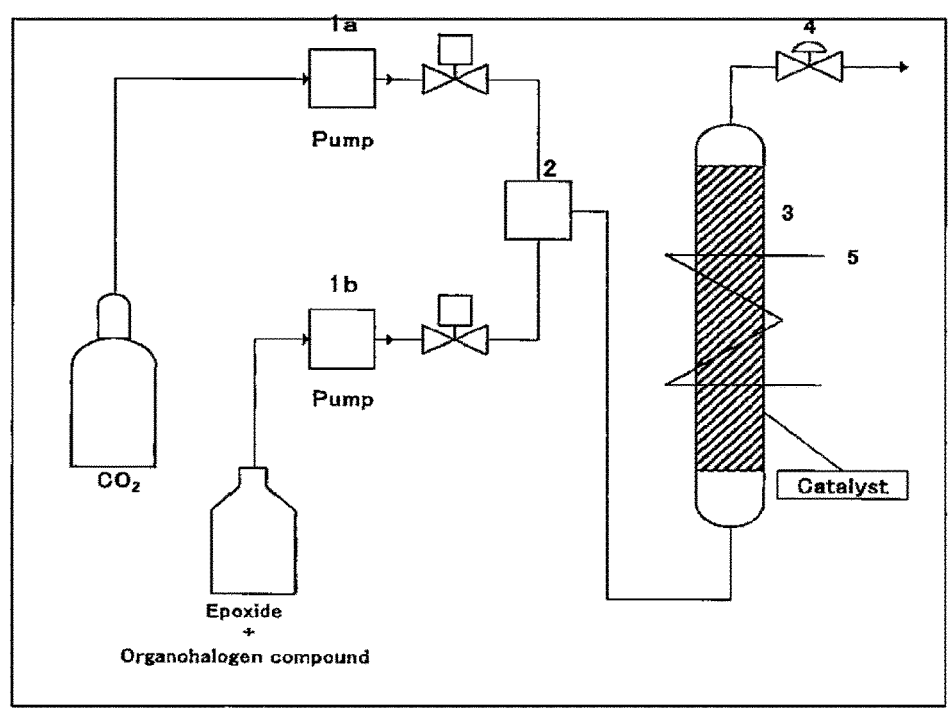
FIG. 1 is a schematic view showing one example of non-circulation type reaction apparatus used in the producing method of the present invention.

The method for producing a cyclic carbonate of the present invention is characterized in that epoxide and carbon dioxide are reacted in the presence of a quaternary onium salt selected from the group consisting of a quaternary ammonium salt having a halogenated anion as a counter ion and a quaternary phosphonium salt having a halogenated anion as a counter ion, or a solid catalyst obtained by immobilizing the quaternary onium salt onto a carrier and, during the reaction, an organohalogen compound containing at least one halogen atom in one molecule is added to the reaction system.

<Epoxide>

Epoxide used in the producing method of the present invention is not particularly limited as long as it contains at least one epoxy ring (3-membered ring containing two carbon atoms and one oxygen atom) in the formula, and examples thereof include ethylene oxide, propylene oxide, butylene oxide, isobutylene oxide, vinylethylene oxide, trifluoromethylethylene oxide, cyclohexene oxide, styrene oxide, butadiene monooxide, butadiene dioxide, 2-methyl-3-phenylbutene oxide, pinene oxide and tetracyanoethylene oxide.

Among these epoxides, an epoxide represented by the following formula (1) is preferable, and ethylene oxide and propylene oxide are more preferable.

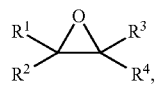

(1)

$R^1$ and $R^2$ each independently represents a hydrogen atom, alkyl having 1 to 6 of carbon atom, haloalkyl having 1 to 6 of carbon atom, alkenyl having 2 to 6 of carbon atom, haloalkenyl having 2 to 6 of carbon atom, aryl having 6 to 12 of carbon atom or cyano, $R^3$ and $R^4$ each independently represents a hydrogen atom, cyano or aryl having 6 to 12 of carbon atom; provided that either $R^3$ or $R^4$ may form cycloalkyl with either $R^1$ or $R^2$.

The number of carbon atoms in the alkyl or the haloalkyl represented by $R^1$ and $R^2$ described above is preferably from 1 to 4. Examples of the alkyl include methyl, ethyl, propyl and butyl, preferably methyl and ethyl, and more preferably methyl.

The number of carbon atoms in the alkenyl or the haloalkenyl represented by $R^1$ and $R^2$ described above is preferably from 2 to 4, and a specific example includes vinyl.

Examples of a halogen atom in the haloalkyl and the haloalkenyl include fluorine, chlorine, bromine and iodine.

For the aryl represented by $R^2$, $R^3$, and $R^4$ described above, phenyl is preferable.

Among $R^1$ and $R^2$ as described above, a hydrogen atom, alkyl having 1 to 6 of carbon atom and haloalkyl having 1 to 6 of carbon atom are preferable.

For $R^3$ and $R^4$, a hydrogen atom is preferable.

A use amount of carbon dioxide in the present invention is usually from 1.0 to 10 molar equivalent, and preferably from 1.1 to 2.0 molar equivalent with respect to the above described epoxide.

<Organohalogen Compound>

An organohalogen compound containing at least one halogen atom in one molecule, which is used in the producing method of the present invention, is a compound having a covalent bond between a carbon atom and a halogen atom. By using such an organohalogen compound, the conversion rate and the yield were improved, and in particular, decrease of catalytic activity over time is suppressed when a solid catalyst described later is used as a catalyst.

As the above described organohalogen compound, examples thereof include a halogenated alcohol, a halogenated phenol, an alkyl halide, an aralkyl halide, a halogenated ether and a carbonyl halide, and a halogenated alcohol and an alkyl halide are preferable from the viewpoints of a yield and inhibition of catalyst degradation. These compounds may be used singly or in a combination of two or more kinds.

As the above described halogenated alcohol, examples thereof include aliphatic monohalogenated alcohols such as chloromethanol, chloroethanol, chloropropanol, chlorobutanol, chloropentanol, bromomethanol, bromoethanol, bromopropanol, bromobutanol, bromopentanol, iodomethanol, iodoethanol and iodopropanol; aliphatic halogenated alcohols each having plural halogen atoms such as dichloromethanol, dichloroethanol, dichloropropanol, dichlorobutanol, dichloropentanol, dibromomethanol, dibromoethanol, dibromopropanol, dibromobutanol, dibromopentanol, diiodomethanol, diiodoethanol, diiodopropanol, trichloromethanol, trichloroethanol, trichloropropanol, trichlorobutanol, trichloropentanol, tribromomethanol, tribromoethanol, tribromopropanol, trichloropentanol, triiodomethanol, triiodoethanol and triiodopropanol; and alicyclic halogenated alcohols such as chlorocyclohexanol, chlorocyclopentanol, bromocyclohexanol and bromocyclopentanol. Among these examples, from the viewpoints of a yield and suppression of catalyst degradation, a monohalogenated alcohol is preferable, an aliphatic monohalogenated alcohol is more preferable, bromoethanol, chloroethanol, bromopropanol and chloropropanol are furthermore preferable, and bromoethanol and bromopropanol are particularly preferable.

Examples of the above described halogenated phenol include monohalogenated phenols such as bromophenol and chlorophenol.

Examples of the above described alkyl halide include aliphatic alkyl monohalides such as chloromethane, chloroethane, 1-chloropropane, 2-chloropropane, 1-chlorobutane, 2-chlorobutane, isobutyl chloride, tert-butyl chloride, chloropentane, bromomethane, bromoethane, 1-bromopropane, 2-bromopropane, isopropyl bromide, 1-bromobutane, 2-bromobutane, isobutyl bromide, tert-butyl bromide, bromopentane, iodomethane, iodoethane and iodopropane; aliphatic alkyl halides each having plural halogen atoms such as dichloromethane, dichloroethane, dichloropropane, dichlorobutane, dichloropentane, dibromomethane, dibromoethane, dibromopropane, dibromobutane, dibromopentane, diiodomethane, diiodoethane, diiodopropane, trichloromethane, trichloroethane, trichloropropane, trichlorobutane, trichloropentane, tribromomethane, tribromoethane, tribromopropane, tribromobutane, tribromopentane, triiodomethane, triiodoethane and triiodopropane; and alicyclic alkyl halides such as chlorocyclohexane, chlorocyclopentane, bromocyclohexane and bromocyclopentane.

Examples of the above described aralkyl halide include chlorobenzyl, bromobenzyl and iodobenzyl.

Examples of the above described halogenated ether include monohalogenated aliphatic ethers such as a chloromethylethyl ether, a bromopropylbutyl ether and an iododipentyl ether; aliphatic ethers each having plural halogen atoms such as a dichlorodimethyl ether, a dibromoethylbutyl ether and a triiodopropylhexyl ether; alicyclic halogenated ethers such as a chloromethylcyclohexyl ether and a bromodicyclopentyl ether; and halogenated aromatic ether compounds such as a bromobenzylmethyl ether.

As the above described carbonyl halide, halogenated ketone and halogenated aldehyde are preferable. Herein, the halogenated ketone means a compound having a structure in which a hydrogen atom contained in ketone is replaced with a halogen atom, and the halogenated aldehyde means a compound having a structure in which a hydrogen atom bonding to α carbon, β carbon, etc. (other than a hydrogen atom which directly bonds to a carbonyl bond) is replaced with a halogen atom.

Specific examples of the above described halogenated ketone include monohalogenated aliphatic ketones such as chloromethylethyl ketone, bromopropylbutyl ketone and iododipentyl ketone; aliphatic ketones each having plural halogen atoms such as dichloroacetone, dibromoethylbuty ketone, and triiodopropylhexyl ketone; alicyclic halogenated ketones such as chloromethylcyclohexyl ketone and bromodicyclopentyl ketone; and halogenated aromatic ketones such as bromobenzylmethyl ketone.

Examples of the above described halogenated aldehyde include chloroacetoaldehyde and bromoacetoaldehyde.

Among organohalogen compounds as described above, an organomonohalogen compound is preferable from the viewpoints of a yield and suppression of catalyst degradation, and an organomonohalogen compound represented by the following formula (2) is more preferable.

R represents linear or branched chain alkyl having 1 to 6 of carbon atom, aralkyl having 7 to 20 of carbon atom, alkoxyalkyl having 2 to 12 of carbon atom, alkanoylalkyl having 3 to 12 of carbon atom, formylalkyl having 2 to 6 of carbon atom or hydroxyalkyl having 1 to 6 of carbon atom, and Z represents a halogen atom.

In the above described formula (2), examples of a halogen atom represented by Z include fluorine, chlorine, bromine and iodine, chlorine and bromine are preferable, and bromine is particularly preferable.

In the formula (2), the number of carbon atoms in alkyl represented by R is preferably from 2 to 4.

Specific examples of the alkyl represented by R include methyl, ethyl, propyl, isopropyl, butyl, sec-butyl, tert-butyl, isobutyl, pentyl and hexyl.

The number of carbon atom in aralkyl represented by R is preferably from 7 to 12, and more preferably from 7 to 10.

Specific examples of the aralkyl represented by R include benzyl, phenethyl, α-methylbenzyl, phenylpropyl, 1-methyl-1-phenylethyl, naphthylmethyl and naphthylethyl.

The number of carbon atom in alkoxyalkyl represented by R preferably from 2 to 8, and more preferably from 2 to 6.

Specific examples of the alkoxyalkyl represented by R include methoxymethyl, methoxyethyl, ethoxymethyl, ethoxyethyl, propoxymethyl, propoxyethyl, butoxymethyl, butoxyethyl, pentyloxymethyl, pentyloxyethyl, hexyloxymethyl and hexyloxyethyl.

The number of carbon atom in alkanoylalkyl represented by R is preferably from 3 to 8, and more preferably from 3 to 6.

Specific examples of the alkanoylalkyl represented by R include acetylmethyl, acetylethyl, propionylmethyl, propionylethyl, butyrylmethyl, butyrylethyl, isobutyrylmethyl, isobutyrylethyl, valerylmethyl, valerylethyl, pivaloylmethyl, and pivaloylethyl.

The number of carbon atom in formylalkyl represented by R is preferably from 2 to 4.

Specific examples of the formylalkyl represented by R include formylmethyl, formylethyl, formylpropyl and formylisopropyl.

The number of carbon atom in hydroxyalkyl represented by R is preferably from 2 to 4.

Specific examples of the hydroxyalkyl represented by R include methoxy, ethoxy, propoxy, an isopropoxy, a butoxy, sec-butoxy and pentoxy.

Among R as described above, linear or branched chain alkyl having 1 to 6 of carbon atom and hydroxyalkyl having 1 to 6 of carbon atom are preferable from the viewpoint of suppression of catalyst degradation.

A use amount of the above described organohalogen compound is usually from $1\times10^{-5}$ to 1 mol with respect to 1 mol of epoxide, preferably from $5\times10^{-5}$ to 1 mol, more preferably from $1\times10^{-4}$ to 0.5 mol, further more preferably from $1\times10^{-3}$ to 0.05 mol, still more preferably from $1.5\times10^{-3}$ to $5\times10^{-3}$ mol, and particularly preferably from $2\times10^{-3}$ to $3.5\times10^{-3}$ from the viewpoints of the yield and suppression of catalyst degradation. According to the producing method of the present invention, even when a use amount of an organohalogen compound is within a small amount as described above, the conversion rate and the yield of cyclic carbonate are improved and degradation of the catalyst over time is suppressed.

A method of adding an organohalogen compound is not particularly limited. An example in the case of a batch type reaction includes a method of previously charging an organohalogen compound together with epoxide and a catalyst described later in an autoclave before the reaction, and examples in the case of a continuous flow reaction include a method of directly continuously supplying an organohalogen compound to a reactor by a pump, etc., a method of dissolving an organohalogen compound into epoxide and carbon dioxide and supplying the reaction solution, and a method of dissolving an organohalogen compound into a substance that is a solvent other than the raw materials and supplying the reaction solution.

<Catalyst>

The producing method of the present invention is carried out in the presence of a quaternary onium salt selected from the group consisting of a quaternary ammonium salt having a halogenated anion as a counter ion and a quaternary phosphonium salt having a halogenated anion as a counter ion or in the presence of a solid catalyst obtained by immobilizing the quaternary onium salt onto a carrier. These materials all act as a catalyst for a synthesis reaction of a cyclic carbonate. When the above described solid catalyst is used, separation from a reaction system is facilitated.

As the above described quaternary onium salt, quaternary organic onium salts are preferable. As a halogen in the above descried halogenated anion, examples thereof include fluorine, chlorine, bromine and iodine.

Among such quaternary onium salts, compounds represented by the following formula (3) are preferable.

$R^5$ represents alkyl, aryl or aralkyl, $R^6$ to $R^8$ each independently represents alkyl, aryl, aralkyl, alkoxyalkyl, aryl having alkoxy as a substituent, or a group in which one or more of hydrogen atom contained in the above groups are replaced with groups containing hetero atoms, X represents a phosphorus atom or a nitrogen atom, and Y represents a halogen atom.

In the formula (3), alkyl represented by $R^5$ and $R^6$ to $R^8$ may be in any state of linear chain, branched chain and a ring, and the number of carbon atom is preferably from 1 to 8, more preferably from 1 to 6, and further more preferably from 2 to 4.

As the above described alkyl, examples thereof include methyl, ethyl, propyl, isopropyl, butyl, isobutyl, pentyl, hexyl, heptyl, octyl and cyclohexyl.

The number of carbon atoms in aryl represented by $R^5$ and $R^6$ to $R^8$ is preferably from 6 to 14, more preferably from 6 to 12, and further more preferably from 6 to 10. Examples thereof include phenyl, naphthyl, anthryl, biphenyl and phenanthryl.

The number of carbon atoms in aralkyl represented by $R^5$ and to $R^8$ is preferably from 7 to 12, and more preferably from 7 to 10. Examples thereof include benzyl, phenethyl, phenylpropyl, naphthylmethyl and naphthylethyl.

Alkoxyalkyl represented by $R^6$ to $R^8$ is preferably alkoxyalkyl having 2 to 8 of carbon atom, and examples thereof include methoxyethyl.

Aryl having an alkoxy as a substituent, which is represented by $R^6$ to $R^8$, is preferably alkoxyaryl having 7 to 14 of carbon atom, and examples thereof include methoxyphenyl and dimethoxyphenyl. The number and the positions of alkoxy contained in the aryl are optional and the number of the alkoxy is preferably from 1 to 4, and more preferably 1 or 2.

In the above described alkyl, aryl, aralkyl, alkoxyalkyl and aryl having an alkoxy as a substituent, which are represented by $R^6$ to $R^8$, one or more hydrogen atoms contained in these groups may be substituted with groups each having a hetero atom.

Examples of the hetero atom include nitrogen, oxygen, phosphorus, sulfur and a halogen atom (such as fluorine).

Examples of the above described group having a hetero atom include nitrogen-containing groups such as amino, hydrazino, nitro, cyano, isocyano and amidino; oxygen-containing groups such as alkanoyl, carboxy, alkoxycarbonyl and hydroxy; phosphorus-containing groups such as phosphanyl, phosphono and phosphinyl; and sulfur-containing groups such as sulfo, sulfanyl, alkylsulfanyl, alkylsulfonyl, alkylsulfonylamino, alkylaminosulfonyl, alkylsulfinyl, alkylaminosulfinyl, alkylsulfinylamino and thiocarboxy.

Among $R^5$ and $R^6$ to $R^8$, alkyl, aryl and aralkyl are preferable, and alkyl is more preferable from the viewpoint of a yield.

Examples of a halogen atom represented by Y include fluorine, chlorine, bromine and iodine, and chlorine and bromine are preferable.

Specific examples of the above described quaternary onium salts preferably include tetraralkyl ammonium salts such as tetraralkyl ammonium chloride and tetraralkyl ammonium bromide; and tetraralkyl phosphonium salts such as tetraralkyl phosphonium chloride and tetraralkyl phosphonium bromide.

When the above described quaternary onium salt is used as a catalyst, an inorganic oxide is preferably used in combination as a co-catalyst from the viewpoints of a conversion rate and a yield. Examples of such an inorganic oxide include the same inorganic oxide used as a carrier described below.

As a carrier used in the case of immobilizing the above described quaternary onium salt, examples thereof include an inorganic oxide carrier and an organic polymer carrier. The shape is preferably particulate, and a porous carrier is favorable.

The above described inorganic oxide carrier preferably contains oxides of silicon, aluminum, titanium, magnesium, zirconium, boron, calcium, zinc, barium, iron, and the like, and one or more among these oxides may be contained. Examples of such oxides include $SiO_2$, $Al_2O_3$, $TiO_2$, $MgO$, $ZrO_2$, $B_2O_3$, $CaO$, $ZnO$, $BaO$ and $Fe_2O_3$.

Specific examples of the inorganic oxide carrier preferably include silica gel (gelated silica), mesoporous silica, ceramics, zeolite and porous glass, and silica gel and mesoporous silica are preferable.

Examples of the above described organic polymer carrier include polystyrene, a polystyrene copolymer, poly(meth)acrylate, poly(meth)acrylamide, polyimide, polybenzimidazole, polybenzoxazole, polybenzothiazole, polyethyelene glycol, polypropylene glycol, or copolymers and polymer blends containing these polymers as main components.

Additionally, in the above described solid catalyst, a quaternary onium salt may be directly bound to a carrier as described in the following formula (4-1), or may be bound to a carrier through a linker as described in the following formula (4-2).

(4-1)

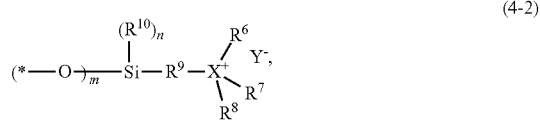

(4-2)

in the formulae (4-1) and (4-2), $R^9$ represents a divalent group derived from $R^5$ described above, $R^{10}$ represents methyl or ethyl, n represents an integer from 0 to 2, m represents an integer from 1 to 3, however, when n+m=3 is satisfied and n is 2, two of $R^{10}$s may be the same or different, * represents a binding site with a carrier, and the other symbols denote the same as described above.

In particular, a quaternary onium salt having a structure of n=0 and m=3 is preferable.

Among the above described catalysts, a solid catalyst obtained by immobilizing a quaternary phosphonium salt having a halogenated anion as a counter ion or a quaternary ammonium salt having a halogenated anion as a counter ion onto a carrier is particularly preferable from the viewpoints of the conversion rate and the yield.

For a solid catalyst obtained by immobilizing a quaternary onium salt onto a carrier, a commercially available one may be used, but, for example, according to methods described in WO 2005/084801 A and JP 2008-296066 A, a solid catalyst may be prepared by reacting a silane compound containing halogen with a silica gel, thereafter allowing the silane compound to react with organic phosphine such as trialkyl phosphine to form into a phosphonium salt, and on the like.

A use amount of the above described catalyst may be suitably adjusted, and is usually from 0.01 to 10 parts by mass with respect to 100 parts by mass of epoxide, and preferably from 0.03 to 10 parts by mass.

An inorganic oxide used as the above described solid catalyst and co-catalyst may be treated by heating before use from 20 to 140° C. (preferably from 50 to 120° C.) under vacuum exhaust or in an inert gas flow such as helium, argon, nitrogen and carbon dioxide, if necessity. Therefore, the yield of a cyclic carbonate can be improved.

The method for producing a cyclic carbonate of the present invention can be carried out either under the presence or absence of a solvent.

As the above described solvent, examples thereof include, in addition to a cyclic carbonate that is the objective compound, aliphatic hydrocarbons such as pentane, hexane and heptane; aromatic hydrocarbons such as benzene and toluene; alcohols such as methanol and ethanol; ketones such as acetone and methyl ethyl ketone; ethers such as a diethyl ether, a methyl-tert-butyl ether, tetrahydrofuran and dioxane; amides such as dimethylformamide and dimethylacetoamide; esters such as ethyl acetate; tertiary amines such as triethylamine, pyridine, methylpyridazine and N,N'-dimethylpyridazinone; sulfides such as dibutyl sulfide; and phosphines such as tributylphosphine. These solvents may be used alone or in combination of two or more kinds.

When a solvent is used, a concentration of epoxide in the reactor as the use amount is usually from 0.1 to 50% by mass, preferably from 0.5 to 40% by mass, and more preferably from 1.0 to 20% by mass.

A reaction temperature in the producing method of the present invention is preferably within the range from 20 to 160° C. more preferably within the range from 50 to 150° C., and further more preferably within the range from 80 to 140° C. from the viewpoint of reaction efficiency.

A reaction pressure is not particularly limited, and preferably within the range from 0.1 to 100 Mpa, more preferably within the range from 0.5 to 50 Mpa, and further more preferably within the range from 1 to 25 MPa.

A reaction type in the producing method of the present invention is not particularly limited, and generally used techniques such as a stirring type and a fixed bed type can be employed. Any method of a batch type, a semi batch type and a continuous flow type may be used.

When the reaction is conducted in a batch type, for example, an organohalogen compound, epoxide and a catalyst are charged into an autoclave equipped with a stirring device, and carbon dioxide is then filled and sealed. Then, while stirring the inside of the autoclave, the autoclave is heated and carbon dioxide is refilled to adjust the internal pressure if needed, and the mixture is thus reacted for a predetermined time, and the generated cyclic carbonate is then separated by a desired technique.

As shown in examples described below, according to the producing method of the present invention, a cyclic carbonate can be effectively produced at a high conversion rate and a high yield and, additionally, degradation of the catalyst over time is suppressed and catalytic activity hardly decreases. Therefore, a catalyst can be used while continuously keeping high activity for a long time, and according to the producing method of the present invention by a continuous flow process using a fixed bed tubular reactor, an amount in use of a catalyst and a renewal cost of the catalyst can be suppressed, and the cyclic carbonate can be industrially advantageously produced in particular.

The above described producing method is a continuous producing method of a cyclic carbonate in which a catalyst is filled in a fixed bed tubular reactor, carbon dioxide and epoxide are continuously supplied into the fixed bed tubular reactor to be brought into contact with the catalyst and, at the same time, the reaction solution in the fixed bed tubular reactor is continuously extracted, and the producing method is characterized in that a solid catalyst obtained by immobilizing a quaternary onium salt selected from the group consisting of a quaternary ammonium salt having a halogenated anion as a counter ion and a quaternary phosphonium salt having a halogenated anion as a counter ion onto a carrier is used as the catalyst, and an organohalogen compound containing at least one halogen atom in a molecule is supplied to the fixed bed tubular reactor. In addition, it is preferable in the continuous producing method of the present invention that carbon dioxide and epoxide are mixed and supplied to the fixed bed tubular reactor.

In the above described producing method, for example, using a flow reactor (FIG. 1) as shown in FIG. 1 in which pumps (1a, 1b), a fluid mixer (2), a reactor (3), a pressure control device (4), a temperature control device (5), and the like, are connected, and an organohalogen compound, epoxide and carbon dioxide may be heated if necessary and continuously reacted in the reactor (3) that is filled with the above described solid catalyst.

An organohalogen compound, and a substance to be a solvent other than epoxide and carbon dioxide which are raw materials may be allowed to co-exist and flow. In addition, a part of a reaction solution continuously extracted from a fixed bed tubular reactor may be supplied to the fixed bed tubular reactor and circulated.

The obtained cyclic carbonate has a structure in which an epoxy ring in the above described epoxide is changed into a carbonate ring (5-membered ring having O—CO—O bond), and examples thereof include ethylene carbonate, propylene carbonate, butylene carbonate, isobutylene carbonate, trifluoromethylethylene carbonate, vinylethylene carbonate, cyclohexene carbonate, styrene carbonate, butadiene monocarbonate, butadiene dicarbonate, chloromethyl carbonate, pinene carbonate, and tetracyanoethylene carbonate. A preferable cyclic carbonate is represented by the following formula (5)

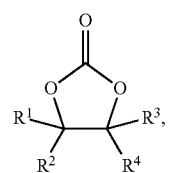

(5)

$R^1$ to $R^4$ denote the same definitions as described above.

The obtained cyclic carbonate may be separated and purified by suitably combining general methods if necessary.

Since an organohalogen compound separated from the cyclic carbonate by separation and purification can also be recovered and used in a reaction again, the cyclic carbonate can be repeatedly obtained at a high conversion rate and a high yield, and low cost and reduction of environmental burdens can be thus expected according to the producing method of the present invention. Either a batch type method or a continuous type method may be employed in these recoveries.

EXAMPLES

Hereinbelow, the present invention will be specifically described by reference to examples, and the present invention is not limited to these examples.

Analytical methods employed in respective examples and comparative examples will be described as follows.

(1) X-Ray Fluorescence Analysis

For measurements of modification amounts of bromine, chlorine and phosphorous in a catalyst, an X-ray fluorescence analysis was used (apparatus: product name "System 3270" (produced by Rigaku Corporation), measurement conditions: Rh tube, tube voltage of 50 kV, cube current of 50 my, vacuum atmosphere, detector: SC, F-PC).

(2) Gas Chromatography

Gas chromatography was employed for composition analysis on a reaction solution. The analytical conditions will be described as follows.

Apparatus: product name "GC-2010 Plus" (manufactured by Shimadzu Corporation)
Detector: FID
INJ temperature: 150° C.
DET temperature: 260° C.
Sample amount: 0.3 μL
Split ratio: 5
Column: DB-624 (60 m, 0.32 mmID, 1.8 μm, manufactured by Agilent Technologies)
Column temperature: 70° C., 3 minutes-5° C./minutes-120° C.-10° C./minutes-250° C., 5 minutes (31 minutes in total)

Catalyst Synthesis Example 1

Synthesis of Tributyl Phosphonium Bromide Surface Modified Silica Gel Catalyst (Catalyst A)

20 g of beaded silica gel (CARiACT Q-10 manufactured by FUJI SILYSIA CHEMICAL LTD. (average pore diameter of 10 nm, particle diameter of 1.2 to 2.4 mm, specific surface area of 300 m$^2$/g)) and 50 mL of 2N hydrochloric acid were charged in a 200 mL-three-neck flask equipped with a stirring blade, the inside of the flask was replaced with nitrogen and refluxed by heating for 4 hours to thus conduct a demetallation treatment on the silica gel. Then, the silica gel was separated by filtration and sufficiently washed with ion exchange water. In addition, an aqueous 1 N-silver nitrate solution was dropped into the solution after washing to confirm that chlorine was not contained and sufficient washing was carried out on the basis that the solution did not become clouded.

The above described silica gel that underwent an acid treatment and 50 mL of toluene were charged in a 200 mL-three-neck flask equipped with a stirring blade, which has a Dean-Stark trap, azeotropic dehydration of toluene-water was carried out for 2 hours under reflux at 110° C. to remove moisture in the silica gel. The moisture content in the toluene solvent in this step was 20 ppm.

The Dean-Stark trap was detached from the 200 mL-three-neck flask equipped with a stirring blade, the inside of the flask was replaced with nitrogen, and 4.8 g of 3-bromopropylmethoxysilane was then dropped thereto. The reaction solution was directly refluxed by heating at 110° C. for 5 hours to thus conduct a silanization reaction.

The obtained reaction product was separated by filtration and washed with 20 mL of acetone five times. It was confirmed that less than 50 ppm of 3-bromopropylmethoxysilane was contained in the solution after washing three times by gas chromatography analysis. The obtained reaction product was contained in a 1 L-flask, and dried under a reduced pressure at 120° C. for 2 hours to obtain a catalyst precursor (bromopropylated silica gel).

The obtained catalyst precursor and 70 mL of xylene were charged into a 200 mL-three-neck flask equipped with a stirring blade, the inside of the flask was replaced with nitrogen and thereto was then dropped 4.4 g of tri-n-butyl phosphine. The reaction solution was directly refluxed by heating at 140° C. for 25 hours to thus conduct a reaction of forming into quaternary phosphonium. After the reaction, the reaction product was separated by filtration and washed with 20 mL of acetone three times. It was confirmed that less than 50 ppm of tri-n-butylphosphine was contained in the solution after washing three times by gas chromatography analysis. The obtained reaction product was contained in a 1 L flask and dried under a reduced pressure at 120° C. for 2 hours to thus obtain a target catalyst A (tributyl phosphonium bromide surface modified silica gel, $SiO_2$—$C_3H_6PBu_3Br$). The bromine modification amount in the catalyst was 0.59 mmol/g, and the phosphorous modification amount was 0.50 mmol/g.

Catalyst Synthesis Example 2

Synthesis of Tributyl Phosphonium Bromide Surface Modified Silica Gel Catalyst (Catalyst B)

2000 g of beaded silica gel (CARiACT Q-10 manufactured by FUJI SILYSIA CHEMICAL LTD. (average pore diameter of 10 nm, particle diameter of 1.2 to 2.4 mm, specific surface area of 300 m$^2$/g)) and 5000 mL of xylene were charged in a 10 L-three-neck flask equipped with a stirring blade, which has a Dean-Stark trap, and azeotropic dehydration of toluene-water was carried out for 2 hours under reflux at 140° C. to remove moisture in the silica gel. Then, the Dean-Stark trap was detached, the inside of the flask was replaced with nitrogen, and 219 g (0.846 mol) of 3-bromopropylmethoxysilane was then dropped thereto. The reaction solution was directly refluxed by heating at 135° C. for 7 hours to thus conduct a silanization reaction. The obtained reaction product was then separated by filtration and washed with xylene twice to thus obtain 3810 g of a catalyst precursor containing xylene (bromopropylated silica gel). Subsequently, the obtained catalyst precursor and 5000 mL of xylene were charged into a 10 L-three-neck flask equipped with a stirring blade, the inside of the flask was replaced with nitrogen, and thereto was then dropped 453 g of tri-n-butyl phosphine. The reaction solution was directly heated at 120° C. for 25 hours, thereby carrying out a reaction of forming into quaternary phosphonium. After the reaction, the reaction product was separated by filtration and washed with acetone six times. The obtained reaction product was dried under a reduced pressure at 120° C. for 5 hours under a nitrogen gas flow to thus obtain 2328 g of a target catalyst B (tributyl phosphonium bromide surface modified silica gel, $SiO_2$—$C_3H_6PBu_3Br$). The bromine modification amount in the catalyst was 0.35 mmol/g, and the phosphorus modification amount was 0.32 mmol/g.

Catalyst Synthesis Example 3

Synthesis of Tributyl Phosphonium Chloride Surface Modified Silica Gel Catalyst (Catalyst C)

Catalyst C (tributyl phosphonium chloride surface modified silica gel, $SiO_2$—$C_3H_6PBu_3Cl$) was synthesized by the same operation as Catalyst Synthesis Example 1 except for replacing 3-bromopropyltrimethoxysilane with 3-chloropropyltrimethoxysilane. The chlorine modification amount in the catalyst was 0.42 mmol/g, and the phosphorus modification amount was 0.33 mmol/g.

Catalyst Synthesis Example 4

Synthesis of Tributyl Phosphonium Bromide Surface Modified Silica Gel Catalyst (Catalyst D)

10 g of the catalyst obtained in Catalyst Synthesis Example 3 was filled in a chromatographic tube, and 175 mL of a methanol solution containing 3.5% by mass of tetramethyl ammonium bromide was gradually circulated. Then, the reaction solution was sufficiently washed with acetone and transferred into a schlenk tube, and degassed and dried at 100° C. to thus obtain a catalyst D (tributyl phosphonium bromide surface modified silica gel, $SiO_2$—$C_3H_6PBu_3Br$). The bromine modification amount in the catalyst was 0.33 mmol/g, the chlorine modification amount was 0.09 mmol/g, and the phosphorus modification amount was 0.32 mmol/g.

Catalyst Synthesis Example 5

Synthesis of Trimethylammonium Bromide Surface Modified Silica Gel Catalyst (Catalyst E)

$SiO_2$—$C_3H_6NMe_3$ $(CO_2)_{1/2}$ (manufactured by Aldrich, loading of 0.7 mmol/g, 200 to 400 mesh), which was surface-modified with trimethylammonium carbonate that was a commercially available reagent, was suspended into ethanol, and thereto was gradually added a methanol solution containing 10% of hydrobromic acid to conduct a neutralization reaction until the pH of the solution reached 4 or less.

The obtained catalyst was collected by filtration, washed with acetone and ether, and then air-dried and vacuum-dried at a temperature from room temperature to 100° C. to thus obtain a target catalyst E (trimethylammonium bromide surface modified silica gel, $SiO_2$—$C_3H_6NMe_3Br$). In results of elemental analysis on the catalyst E, bromine was 0.58 mmol/g, nitrogen was 0.60 mmol/g, carbon was 4.25 mmol/g, and hydrogen was 14.9 mmol/g.

Catalyst Synthesis Example 6

Synthesis of Tributyl Phosphonium Bromide Surface Modified Polystyrene Resin Catalyst (Catalyst F)

5.0 g of a commercially available 4-chloromethyl group-containing beaded polystyrene resin, PS—$C_6H_4CH_2Cl$ (manufactured by Argonaut Technologies, Inc., ArgoPore-Cl, 0.98 mmol-Cl/g) was suspended into 90 mL of toluene under an argon atmosphere, and 500 mg of tributylphosphine was added while gradually stirring in a 200 mL-three-neck flask equipped with a stirring blade. The suspension was reacted at 110° C. for one week while stir the suspension was continued under an argon atmosphere. The solution was separated by filtration from the suspended product after the reaction, and the obtained solid was sequentially washed with methanol, acetone and ether, air-dried and then dried at room temperature under vacuum at 1 torr or less for 6 hours to thus obtain a tributyl phosphonium chloride surface modified polystyrene resin, PS—$C_6H_4CH_2PBu_3Cl$. The chlorine modification amount of the obtained polystyrene resin was 1.0 mmol/g, and the phosphorous modification amount was 0.72 mmol/g.

The reaction product was filled in a chromatographic tube, and 175 mL of a methanol solution containing 3.5% by mass of tetramethylammonium bromide was gradually circulated. After the completion, the reaction product was sufficiently washed with methanol, acetone and ether in series. The reaction product was transferred into a schlenk tube and degassed and dried at 100° C. to obtain a target catalyst F (tributyl phosphonium bromide surface modified polystyrene resin, PS—$C_6H_4CH_2PBu_3Br$). The bromine modification amount in the catalyst was 0.8 mmol/g, the chlorine modification amount was 0.05 mmol/g, and the phosphorous modification amount was 0.7 mmol/g.

Example 1

Producing Example of Propylene Carbonate (1)

Propylene carbonate was produced using a continuous flow reactor shown in FIG. 1.

That is, 2 g of the catalyst A was filled in a reactor 3 having an internal diameter of 18 mm, a length of 40 cm and a volume of 100 mL and stainless balls each having a particle diameter of 2 mm were further filled in the front and rear of the catalyst. Then, liquefied carbon dioxide was supplied into the reactor 3 at 0.1 mL/min by a pump 1a. Subsequently, the reactor pressure was adjusted at 7 Mpa by a back-pressure regulating valve 4 installed in the downstream of the reactor 3, the temperature of the reactor 3 was increased to 100° C. in an aluminum casing furnace 5, and carbon dioxide continued to be directly flown for 2 days to dry the catalyst. Then, a supply of carbon dioxide into the reactor 3 was increased to 0.3 mL/min by the pump 1a. A raw material mixture of propylene oxide, propylene carbonate and 2-bromoethanol, which was previously adjusted to have a volume ratio of 1:1:0.002 (2-bromoethanol/propylene oxide=2.0 mmol/mol), was supplied to the reactor 3 at 0.1 mL/min by a pump 1b to thus initiate a continuous flow reaction.

A conversion rate of propylene oxide after passing 200 hours from the initiation of the reaction was 55%, the yield of propylene carbonate was 55%, and the selection ratio was 99.9% or more. Results are shown in Table 1.

Examples 2 to 6

Producing Examples of Propylene Carbonates (2) to (6)

Propylene carbonates were produced in the same operation as Example 1 except for the change in a volume ratio of propylene oxide, propylene carbonate and 2-bromoethanol in the adjustment of raw materials in a continuous flow reaction to 1:1:0.001 (Example 2), 1:1:0.0006 (Example 3), 1:1:0.0002 (Example 4), 1:1:0.005 (Example 5), 1:1:0.01 (Example 6) (2-bromoethanol/propylene oxide=1.0 (Example 2), 0.6 (Example 3), 0.2 (Example 4), 5 (Example 5), 10 (Example 6) mmol/mol). Results are shown in Table 1.

Example 7

Evaluation of Catalyst after Continuous Flow Reaction in Example 1

Analysis by fluorescent X-ray was carried out on the catalyst after completion of a continuous flow reaction in Example 1. As a result, the bromine modification amount was 0.47 mmol/g, and the phosphorus modification amount was 0.41 mmol/g.

Subsequently, when residual ratios of bromine and phosphorus on the catalyst were found according to the following formula, the bromine residual ratio was 80%, and the phosphorus residual ratio was 81%.

Bromine residual ratio=(bromine modification amount of catalyst after reaction/bromine modification amount of catalyst before reaction)×100

Phosphorus residual ratio=(phosphorus modification amount of catalyst after reaction/phosphorus modification amount of catalyst before reaction)×100

Furthermore, from the catalyst after completion of the reaction in Example 1 described above, propylene carbonate was synthesized in a batch type, and the activity of the catalyst was evaluated.

That is, a 50 mL-autoclave containing a stirrer was charged with 200 mg of the catalyst taken out after the continuous reaction in Example 1 and the catalyst was dried under a reduced pressure at 120° C. for 1 hour. The inside of the autoclave was returned to atmospheric pressure and room temperature with nitrogen and then charged with 4 mL (57 mmol) of propylene oxide. Subsequently, carbon dioxide was temporarily filled up to 1.5 MPa, the inside of the autoclave was then heated to 120° C. while stirring at 800 rpm by a rotator, and carbon dioxide was further filled to thus adjust the internal pressure at 4.5 Mpa and the reaction mixture was allowed to react for 1 hour. After cooling, remaining carbon dioxide was released to depressurize the inside of the autoclave. The obtained reaction solution was analyzed by gas chromatography. The conversion rate of propylene oxide was 41.0%, the yield of propylene carbonate was 41.0, and the selection ratio was 99.9%. Results are shown in Table 1.

Examples 8 to 12

Evaluation of Catalysts after Continuous Reactions in Examples 2 to 6

Catalysts were evaluated in the same operation as Example 7 except for replacing the catalyst after completion of the continuous flow reaction in Example 1 with the catalysts after completion of the continuous flow reactions in Examples 2 to 6. Results are shown in Table 1.

Comparative Example 1

Producing Example of Propylene Carbonate (7)

Propylene carbonate was produced in the same operation as Example 1 except for replacing the raw material mixture with a raw material mixture that was previously adjusted to have a volume ratio of propylene oxide and propylene carbonate of 1:1 without adding 2-bromoethanol for the raw material in a continuous flow reaction. Results are shown in Table 1.

Comparative Example 2

Evaluation of Catalyst after Continuous Reaction in Comparative Example 1

A catalyst was evaluated in the same operation as Example 7 except for replacing the catalyst after completion of the continuous flow reaction in Example 1 with the catalyst after completion of the continuous flow reaction in Comparative Example 1. Results are shown in Table 1.

Comparative Example 3

Batch Type Reaction of Catalyst Before Reaction

A catalyst was evaluated in the same operation as Example 7 except for replacing the catalyst after completion of the continuous flow reaction in Example 1 with an unused catalyst A. Results are shown in Table 1.

TABLE 1

| | | Continuous flow reaction | | | Fluorescent X-ray analysis of catalyst after reaction | | | | Results of batch reaction | |
|---|---|---|---|---|---|---|---|---|---|---|
| | | Reaction | Reaction result | | | | | | | |
| | | condition BrEtOH/PO (mmol/mol) | Conversion rate (%) | Yield (%) | Br amount (mmol/g) | Br residual ratio (%) | P amount (mmol/g) | P residual ratio (%) | Conversion rate (%) | Yield (%) |
| | Examples 1, 7 | 2.0 | 55 | 55 | 0.47 | 80 | 0.41 | 81 | 41.0 | 41.0 |
| | Examples 2, 8 | 1.0 | 49 | 49 | 0.46 | 78 | 0.40 | 79 | 35.5 | 35.5 |
| | Examples 3, 9 | 0.6 | 39 | 39 | 0.45 | 76 | 0.40 | 79 | 28.8 | 28.8 |
| | Examples 4, 10 | 0.2 | 30 | 30 | 0.42 | 72 | 0.39 | 77 | 25.5 | 25.5 |
| | Examples 5, 11 | 5 | 58 | 58 | 0.48 | 81 | 0.41 | 82 | 40.9 | 40.9 |
| | Examples 6, 12 | 10 | 62 | 62 | 0.53 | 90 | 0.45 | 90 | 41.2 | 41.2 |
| | Comparative Examples 1, 2 | — | 20 | 20 | 0.25 | 42 | 0.31 | 63 | 24.5 | 24.5 |
| | Comparative Example 3 | — | — | — | — | — | — | — | 42.7 | 42.6 |

In the table, BrEtOH denotes 2-bromoethanol, PO denotes propylene oxide, Br denotes a bromine atom, and P denotes a phosphorus atom.

As shown in Table 1, it was confirmed that Examples 1 to 6, in which bromoethanol was added, showed higher conversion rates and yields in continuous flow reactions as compared to Comparative Example 1, in which bromoethanol was not added.

As bromine residual ratios of the catalysts after reactions were compared, the residual ratio of bromine in Comparative Example 2, in which bromoethanol was not added, was 42%, which was significantly reduced; in contrast, Examples 7 to 12, in which bromoethanol were added, all showed high residual ratios such as 70% or more. What is more, when conversion rates of the catalysts after reactions in batch type reactions were compared, while the conversion rate of the unused product (Comparative Example 3) was 42.6%, the conversion rate was decreased to 24.5% in Comparative Example 2 without adding bromoethanol. In contrast, the degree of decrease in conversion rates and yields was smaller in Examples 7 to 12, in which bromoethanol was added. It was found from the results that when a cyclic carbonate was produced by adding bromoethanol, catalytic activity hardly decreases.

Example 13

Producing Example of Ethylene Carbonate (1)

Figure 2:
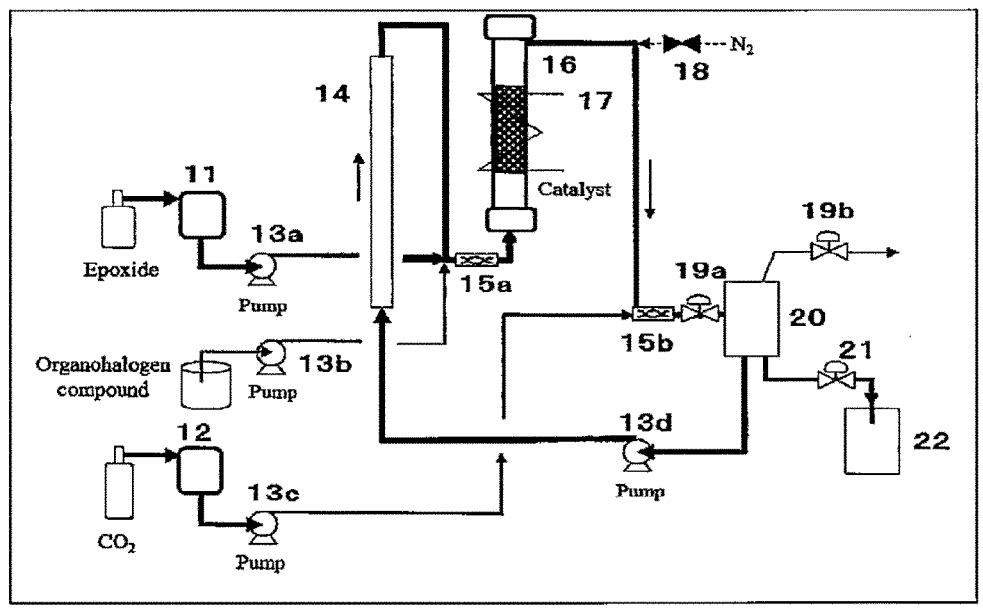
FIG. 2 is a schematic view showing one example of a circulation type reaction apparatus used in the producing method of the present invention.

An ethylene carbonate was produced using a continuous flow reactor shown in FIG. 2.

That is, 530 g (1000 mL) of the catalyst B was filled in the reactor 16 having an internal diameter of 50 mm, a length of 100 cm and a volume of 2000 mL, and glass beads each having a particle diameter of 4 mm were further filled in the front and rear of the catalyst.

Subsequently, the valve 18 was opened, nitrogen was supplied to the reactor 16 at 1 L/min, and boiled water was further flown into the reactor jacket 17 to increase the temperature of the reactor 16 to 100° C. After nitrogen continued to be directly flown for 8 hours and the catalyst was dried, the valve 18 was closed to terminate drying of the catalyst.

Then ethylene oxide was charged in the ethylene oxide storage tank 11 and carbon dioxide was charged in the carbon dioxide storage tank 12, respectively. 7 kg of ethylene carbonate, which was previously heated at 70° C. to be dissolved, was subsequently charged in a gas-liquid separation tank 20, and the ethylene carbonate was sent to the preheater 14 and the reactor 16 at 1200 g/h by the pump 13d to be circulated. In this procedure, the ethylene carbonate that was supplied to the reactor 16 was heated at a temperature at which the reactor inlet temperature was 100° C. by the preheater 14.

Then, carbon dioxide was supplied to the reactor 16 at 300 g/h by the pump 13c, pressures of the gas-liquid separation tank 20, the preheater 14 and the reactor 16 were adjusted at 7 MP by the back-pressure regulating valve 19b. In this procedure, carbon dioxide was stirred by a static mixer 15b to be dissolved into ethylene carbonate, and carbon dioxide in the state of being dissolved into ethylene carbonate was supplied to the preheater 14 and the reactor 16.

Then, a flow rate of carbon dioxide was adjusted at 45 g/h and a flow rate of ethylene carbonate in which carbon dioxide was dissolved was adjusted at 1,400 g/h by the pumps 13c and 13d, respectively, and pressures of the preheater 14 and the reactor 16 were adjusted at 7.5 MPa by the back-pressure regulating valve 19a.

Subsequently, 2-bromoethanol was supplied to the reactor 16 at 0.43 g/h by the pump 13b, and ethylene oxide was then supplied to the reactor 16 at 30 g/h by the pump 13a to thus initiate a continuous flow reaction.

In supplying 2-bromoethanol and ethylene oxide, 2-bromoethanol and ethylene oxide were mixed with ethylene carbonate by a static mixer 15a and the mixture was supplied to the reactor 16. That is, ethylene oxide, carbon dioxide and 2-bromoethanol altogether were supplied to the reactor 16 with themselves being dissolved in ethylene carbonate. By thus circulating ethylene carbonate, a reaction state can be deemed as a pseudo-liquid-solid reaction with a catalyst.

After passing 6 hours from initiation of the reaction, in order to keep the supply of 2-bromoethanol to the reactor 16 constant at 2-bromoethanol/ethylene oxide 5 mmol/mol, the flow rate of 2-bromoethanol was adjusted at 0.024 g/h by the pump 13b and the reaction was continued. Ethylene carbonate generated by the reaction was extracted to the receiving tank 22 by the liquid level control valve 21.

Figure 3:
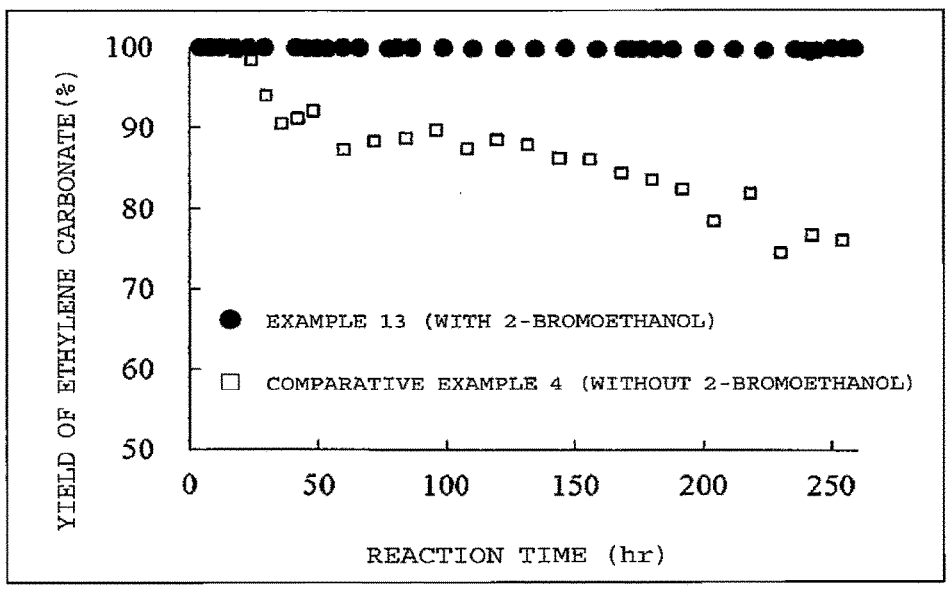
FIG. 3 is a view showing change in the yield of ethylene carbonate over time according to the producing method of Example 13.

The obtained reaction solution was analyzed by gas chromatography at predetermined time intervals to find the yield of ethylene carbonate. Results are shown in FIG. 3.

Comparative Example 4

Producing Example of Ethylene Carbonate (2)

Ethylene carbonate was synthesized in the same operation as Example 13 except for not supplying 2-bromoethanol by the pump 13b. Results are shown in FIG. 3.

Example 14

Producing Example of Propylene Carbonate (8)

A 50 mL-autoclave containing a stirrer was charged with 200 mg of the catalyst A and the catalyst was dried under a reduced pressure at 120° C. for 1 hour. The inside of the autoclave was returned to atmospheric pressure and room temperature with nitrogen and then charged with 0.57 mmol of 2-bromoethano and 4 mL (57 mmol) of propylene oxide.

Subsequently, carbon dioxide was temporarily filled up to 1.5 MPa, the inside of the autoclave was then heated to 120° C. while stirring at 800 rpm by a rotator, and carbon dioxide was further filled to adjust the internal pressure at 4.5 Mpa and the reaction mixture was allowed to react for 1 hour. After cooling, remaining carbon dioxide was released to depressurize the inside of the autoclave. The obtained reaction solution was analyzed by gas chromatography to find the conversion rate of propylene oxide and the yield of propylene carbonate. Results are shown in Table 2.

Example 15

Producing Example of Propylene Carbonate (9)

Propylene carbonate was produced by a batch type reaction in the same procedure as Example 14 except for replacing 2-bromoethanol with bromopropanol (mixture of 2-bromo-1-propanol and 1-bromo-2-propanol, the same shall apply hereinafter). Results are shown in Table 2.

Examples 16 to 21

Producing Examples of Propylene Carbonates (10) to (15)

Propylene carbonate was produced by a batch type reaction in the same procedure as Example 14 except for replacing 2-bromoethanol with tert-butyl bromide (Example 16), isobutyl bromide (Example 17), isopropyl bromide (Example 18), 2-bromobutane (Example 19), bromoethane (Example 20) and 1-bromobutane (Example 21), respectively. Results are shown in Table 2.

Example 22

Producing Example of Propylene Carbonate (16)

Propylene carbonate was produced by a batch type reaction in the same procedure as Example 15 except for replacing the catalyst A with the catalyst C. Results are shown in Table 2.

Example 23

Producing Example of Propylene Carbonate (17)

Propylene carbonate was produced by a batch type reaction in the same procedure as Example 15 except for replacing the catalyst A with the catalyst E. Results are shown in Table 2.

Example 24

Producing Example of Propylene Carbonate (18)

Propylene carbonate was produced by a batch type reaction in the same procedure as Example 15 except for replacing the catalyst A with the catalyst F. Results are shown in Table 2.

Example 25

Producing Example of Propylene Carbonate (19)

Propylene carbonate was produced by a batch type reaction in the same procedure as Example 15 except for replacing the catalyst A with 193 mg (0.57 mmol, 1 mol % of propylene oxide) of commercially available tetrabutyl phosphonium bromide (produced by Aldrich). Results are shown in Table 2.

Example 26

Producing Example of Propylene Carbonate (20)

Propylene carbonate was produced by a batch type reaction in the same procedure as Example 15 except for replacing the catalyst A with a system of a combination use of 200 mg of beaded silica gel (CARiACT Q-10 produced by FUJI SILYSIA CHEMICAL LTD., average pore diameter of 10 nm, particle diameter of 1.2 to 2.4 mm, specific surface area of 300 $m^2/g$) and 193 mg (0.57 mmol, 1 mol % of propylene oxide) of tetrabutyl phosphonium bromide (produced by Aldrich). Results are shown in Table 2.

Example 27

Producing Example of Propylene Carbonate (21)

Propylene carbonate was produced by a batch type reaction in the same procedure as Example 15 except for replacing the catalyst A with 275 mg (0.57 mmol, 1 mol % of propylene oxide) of commercially available tetrabutyl ammonium bromide (produced by Aldrich). Results are shown in Table 2.

Example 28

Producing Example of Propylene Carbonate (22)

Propylene carbonate was produced by a batch type reaction in the same procedure as Example 15 except for replacing the catalyst A with a system of a combination use of 200 mg of beaded silica gel (CARiACT Q-10 produced by FUJI SILYSIA CHEMICAL LTD., average pore diameter of 10 nm, particle diameter of 1.2 to 2.4 mm, specific surface area of 300 $m^2/g$) and 275 mg (0.57 mmol, 1 mol % of propylene oxide) of tetrabutyl ammonium bromide (produced by Aldrich). Results are shown in Table 2.

Comparative Example 5

Producing Example of Propylene Carbonate (23)

Propylene carbonate was produced by a batch type reaction in the same procedure as Comparative Example 3 except for replacing the catalyst A with the catalyst C. Results are shown in Table 2. Results of Comparative Example 3 are also shown in Table 2.

Comparative Example 6

Producing Example of Propylene Carbonate (24)

Propylene carbonate was produced by a batch type reaction in the same procedure as Comparative Example 3 except for replacing the catalyst A with the catalyst E. Results are shown in Table 2.

Comparative Example 7

Producing Example of Propylene Carbonate (25)

Propylene carbonate was produced by a batch type reaction in the same procedure as Comparative Example 3 except for replacing the catalyst A with the catalyst F. Results are shown in FIG. 2.

Comparative Example 8

Producing Example of Propylene Carbonate (26)

Propylene carbonate was produced by a batch type reaction in the same procedure as Example 25 except that bromopropanol was not added. Results are shown in Table 2.

Comparative Example 9

Producing Example of Propylene Carbonate (27)

Propylene carbonate was produced by a batch type reaction in the same procedure as Example 26 except that bromopropanol was not added. Results are shown in Table 2.

Comparative Example 10

Producing Example of Propylene Carbonate (28)

Propylene carbonate was produced by a batch type reaction in the same procedure as Example 27 except that bromopropanol was not added. Results are shown in Table 2.

Comparative Example 11

Producing Example of Propylene Carbonate (29)

Propylene carbonate was produced by a batch type reaction in the same procedure as Example 28 except that bromopropanol was not added. Results are shown in Table 2.

TABLE 2

| | Catalyst | Organohalogen compound | Conversion rate (%) | Yield (%) |
|---|---|---|---|---|
| Example 14 | Catalyst A | 2-bromoethanol | 65.1 | 65.1 |
| Example 15 | Catalyst A | bromopropanol | 70.1 | 70.1 |
| Example 16 | Catalyst A | tert-butyl bromide | 61.4 | 59.5 |
| Example 17 | Catalyst A | isobutyl bromide | 47.9 | 47.8 |
| Example 18 | Catalyst A | isopropyl bromide | 47.8 | 47.7 |
| Example 19 | Catalyst A | 2-bromobutane | 47.6 | 47.5 |
| Example 20 | Catalyst A | bromoethane | 46.7 | 46.6 |
| Example 21 | Catalyst A | 1-bromobutane | 45.2 | 45.1 |
| Comparative Example 3 | Catalyst A | None | 42.7 | 42.6 |
| Example 22 | Catalyst C | bromopropanol | 75.0 | 74.8 |
| Comparative Example 5 | Catalyst C | None | 23.7 | 23.6 |
| Example 23 | Catalyst E | bromopropanol | 92.0 | 91.9 |
| Comparative Example 6 | Catalyst E | None | 43.4 | 43.3 |
| Example 24 | Catalyst F | bromopropanol | 45.9 | 45.8 |
| Comparative Example 7 | Catalyst F | None | 16.1 | 16.0 |
| Example 25 | PBu$_4$Br | bromopropanol | 75.9 | 75.9 |
| Comparative Example 8 | PBu$_4$Br | None | 30.5 | 30.5 |
| Example 26 | PBu$_4$Br + SiO$_2$ | bromopropanol | 93.0 | 92.8 |
| Comparative Example 9 | PBu$_4$Br + SiO$_2$ | None | 61.9 | 61.7 |
| Example 27 | NBu$_4$Br | bromopropanol | 73.0 | 73.0 |
| Comparative Example 10 | NBu$_4$Br | None | 28.1 | 28.1 |
| Example 28 | NBu$_4$Br + SiO$_2$ | bromopropanol | 92.7 | 92.6 |
| Comparative Example 11 | NBu$_4$Br + SiO$_2$ | None | 62.0 | 61.8 |

Example 29

Producing Example of Propylene Carbonate (30)

First, a continuous flow reaction was carried out in the same operation as Comparative Example 1 from the initiation of the reaction to 180 hours except for replacing the catalyst A with the catalyst D, after passing 180 hours from the reaction initiation, the raw material mixture to be supplied was shifted to a raw material mixture that was previously adjusted to have a volume ratio of propylene oxide, propylene carbonate and 2-bromoethanol of 1:1:0.002 (2-bromoethanol/propylene oxide=2.0 mmol/mol).

Figure 4:
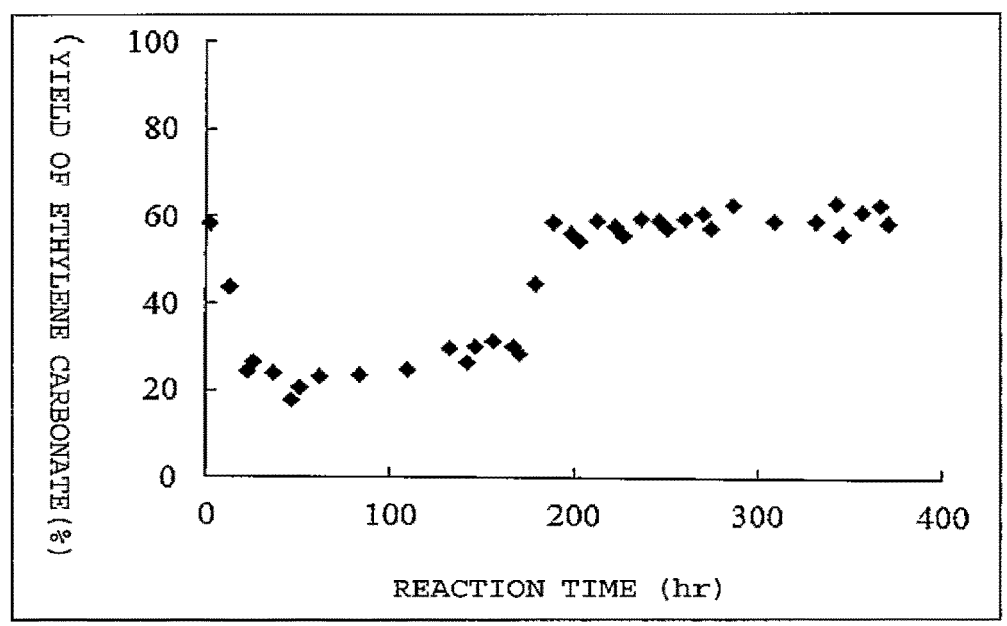
FIG. 4 is a view showing change in the yield of propylene carbonate over time according to the producing method of Example 29.

Although the yield of propylene carbonate after passing 180 hours from the reaction initiation was 30%, the yield was improved up to 60% after passing 200 hours from the reaction initiation, and reduction of the yield of propylene carbonate was not observed even after passing 370 hours from the reaction initiation. Change in the yields of propylene carbonate is shown in FIG. 4.

The catalyst after completion of the continuous flow reaction described above was analyzed by fluorescent X-ray. The bromine modification amount was 0.21 mmol/g, and the phosphorus modification amount was 0.21 mmol/g. The chlorine modification amount was less than the detection limit.

As residual ratios of a halogen element and phosphorus on the catalyst was calculated according to the following formula, the bromine residual ratio was 50%, and the phosphorus residual ratio was 68%.

Halogen residual ratio={bromine modification amount of catalyst after reaction/(bromine modification amount of catalyst before reaction+chlorine modification amount of catalyst before reaction)}×100

Phosphorus residual ratio=(phosphorus modification amount of catalyst after reaction/phosphorus modification amount of catalyst before reaction)×100

As shown in examples described above, in a synthesis of a cyclic carbonate obtained by reacting epoxide and carbon dioxide, the yield was improved and reduction of catalytic activity was significantly suppressed by adding an organohalogen compound.

REFERENCE SIGNS LIST 1a to 1b, 13a to 13d: Pumps
2: Fluid mixer
3, 16: Reactors
4: Pressure control device
5: Temperature control device
11: Ethylene oxide storage tank
12: Carbon dioxide storage tank
14: Preheater
15a and 15b: Static mixers
17: Reactor jacket
18: Valve
19a to 19b: Back-pressure regulating valves
20: Gas-liquid separation tank
21: Liquid level control valve
22: Receiving tank

The invention claimed is:

1. A method for producing a cyclic carbonate comprising:
  (i) reacting epoxide and carbon dioxide in the presence of a quaternary onium salt selected from the group consisting of a quaternary ammonium salt having a halogenated anion as a counter ion and a quaternary phosphonium salt having a halogenated anion as a counter ion, or
  (ii) reacting epoxide and carbon dioxide in the presence of a solid catalyst obtained by immobilizing the quaternary onium salt onto a carrier; and
  adding an organohalogen compound to (i) or (ii);
  wherein the organohalogen compound is represented by the following formula (2):

$$RZ \qquad (2),$$

wherein R represents linear or branched chain alkyl having 1 to 6 of carbon atom, aralkyl having 7 to 20 of carbon atom, alkoxyalkyl having 2 to 12 of carbon atom, alkanoylalkyl having 3 to 12 of carbon atom, formylalkyl having 2 to 6 of carbon atom, or hydroxyalkyl having 1 to 6 of carbon atom, and Z represents a halogen atom,
  wherein the organohalogen compound of formula (2) is a different compound compared to the epoxide.

2. The method according to claim 1, wherein R represents linear or branched chain alkyl having 1 to 6 of carbon atom, or hydroxyalkyl having 1 to 6 of carbon atom.

3. The method according to claim 1, wherein Z represents a bromine atom.

4. The method according to claim 1, wherein the carrier is an inorganic oxide carrier.

5. The method according to claim 1, wherein the epoxide is a compound represented by the following formula (1):

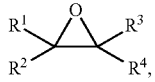
(1)

wherein $R^1$ and $R^2$ each independently represents a hydrogen atom, alkyl having 1 to 6 of carbon atom, haloalkyl having 1 to 6 of carbon atom, alkenyl having 2 to 6 of carbon atom, haloalkenyl having 2 to 6 of carbon atom, aryl having 6 to 12 of carbon atom or cyano, and $R^3$ and $R^4$ each independently represents a hydrogen atom, cyano or aryl having 6 to 12 of carbon atom; or either $R^3$ or $R^4$ form cycloalkyl together with either $R^1$ or $R^2$.

6. A method for continuously producing a cyclic carbonate comprising:
filling a catalyst in a fixed bed tubular reactor and continuously supplying carbon dioxide and epoxide to the fixed bed tubular reactor to be brought into contact with the catalyst and, at the same time, continuously extracting the reaction solution contained in the fixed bed tubular reactor, wherein the catalyst comprises a solid catalyst obtained by immobilizing a quaternary onium salt selected from the group consisting of a quaternary ammonium salt having a halogenated anion as a counter ion and a quaternary phosphonium salt having a halogenated anion as a counter ion onto a carrier, and supplying to the fixed bed tubular reactor an organohalogen compound-represented by the following formula (2):

RZ   (2), wherein R represents linear or branched chain alkyl having 1 to 6 of carbon atom, aralkyl having 7 to 20 of carbon atom, alkoxyalkyl having 2 to 12 of carbon atom, alkanoylalkyl having 3 to 12 of carbon atom, formylalkyl having 2 to 6 of carbon atom or hydroxyalkyl having 1 to 6 of carbon atom, and Z represents a halogen atom.

7. The method according to claim 6, wherein R represents linear or branched chain alkyl having 1 to 6 of carbon atom or hydroxyalkyl having 1 to 6 of carbon atom.

8. The method according to claim 6, wherein Z represents a bromine atom.

9. The method according to claim 6, wherein the carrier is an inorganic oxide carrier.

10. The method according to claim 6, wherein the epoxide is a compound represented by the following formula (1):

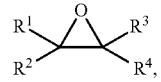
(1)

wherein $R^1$ and $R^2$ each independently represents a hydrogen atom, alkyl having 1 to 6 of carbon atom, haloalkyl having 1 to 6 of carbon atom, alkenyl having 2 to 6 of carbon atom, haloalkenyl having 2 to 6 of carbon atom, aryl having 6 to 12 of carbon atom or cyano, $R^3$ and $R^4$ each independently represents a hydrogen atom, cyano or aryl having 6 to 12 of carbon atom; or either $R^3$ or $R^4$ form cycloalkyl together with either $R^1$ or $R^2$.

11. The method according to claim 6, wherein a part of the reaction solution obtained by continuously extracting from the fixed bed tubular reactor is supplied to the fixed bed tubular reactor to be circulated.

12. The method according to claim 1, wherein the amount of the organomonohalogen is $1 \times 10^{-5}$ to 1 mol with respect to 1 mol of the epoxide.

13. The method according to claim 2, wherein Z represents fluorine atom, a chlorine atom, a bromine atom or an iodine atom.

14. A method for producing a cyclic carbonate comprising:
(i) reacting epoxide and carbon dioxide in the presence of a quaternary onium salt selected from the group consisting of a quaternary ammonium salt having a halogenated anion as a counter ion and a quaternary phosphonium salt having a halogenated anion as a counter ion, or
(ii) reacting epoxide and carbon dioxide in the presence of a solid catalyst obtained by immobilizing the quaternary onium salt onto a carrier; and
adding an organohalogen compound to (i) or (ii), wherein the organomonohalogen compound is a monohalogenated alcohol selected from the group consisting of chloromethanol, chloroethanol, chloropropanol, chlorobutanol, chloropentanol, bromomethanol, bromopropanol, bromobutanol, bromoethanol, bromopentanol, iodomethanol, iodoethanol, and iodopropanol.

15. The method according to claim 14, wherein the organomonohalogen compound is a monohalogenated alcohol selected from the group consisting of bromoethanol, chloroethanol, bromopropanol, and chloropropanol.

* * * * *